(12) United States Patent
Krishnan et al.

(10) Patent No.: US 9,919,150 B2
(45) Date of Patent: Mar. 20, 2018

(54) MECHANISM, SYSTEM, METHOD FOR IN VIVO LEAD FIXATION

(71) Applicant: Subramaniam Chitoor Krishnan, Sacramento, CA (US)

(72) Inventors: Subramaniam Chitoor Krishnan, Sacramento, CA (US); Nitin Patil, Albany, NY (US)

( * ) Notice: Subject to any disclaimer, the term of this patent is extended or adjusted under 35 U.S.C. 154(b) by 0 days.

(21) Appl. No.: 14/385,091

(22) PCT Filed: Mar. 15, 2013

(86) PCT No.: PCT/IB2013/052101
§ 371 (c)(1),
(2) Date: Sep. 12, 2014

(87) PCT Pub. No.: WO2013/136312
PCT Pub. Date: Sep. 19, 2013

(65) Prior Publication Data
US 2015/0045867 A1     Feb. 12, 2015

Related U.S. Application Data

(60) Provisional application No. 61/611,016, filed on Mar. 15, 2012.

(51) Int. Cl.
*A61N 1/05* (2006.01)
*A61N 1/37* (2006.01)

(52) U.S. Cl.
CPC ............. *A61N 1/059* (2013.01); *A61N 1/05* (2013.01); *A61N 1/057* (2013.01); *A61N 1/371* (2013.01); *A61N 1/3706* (2013.01); *A61N 2001/0585* (2013.01)

(58) Field of Classification Search
None
See application file for complete search history.

(56) References Cited

U.S. PATENT DOCUMENTS

| | | | |
|---|---|---|---|
| 6,501,994 B1 | 12/2002 | Janke et al. | |
| 2005/0070981 A1* | 3/2005 | Verma | A61N 1/057 607/112 |
| 2005/0171582 A1* | 8/2005 | Matlock | A61B 18/1485 607/96 |
| 2007/0203554 A1* | 8/2007 | Kaplan | A61N 1/0587 607/119 |
| 2008/0183257 A1 | 7/2008 | Imran et al. | |
| 2010/0023088 A1 | 1/2010 | Stack et al. | |

(Continued)

FOREIGN PATENT DOCUMENTS

WO   WO 2012/030393   3/2012

*Primary Examiner* — Ankit D Tejani
(74) *Attorney, Agent, or Firm* — Snell & Wilmer LLP

(57) ABSTRACT

A lead for in vivo procedures for stimulation of a tissue is provided that has stimulating electrodes and a fixation mechanism disposed at a distal end of the lead. The fixation mechanism includes a fixation component disposed on an opposite side with respect to an active surface of the stimulation electrodes. The lead fixation mechanism when deployed disposes the active surface of stimulation electrodes onto a tissue region opposite to the fixation component. A system and a method for optimally positioning the lead for stimulation of the tissue are also provided.

17 Claims, 12 Drawing Sheets

(56) References Cited

U.S. PATENT DOCUMENTS

| | | | |
|---|---|---|---|
| 2010/0191236 A1* | 7/2010 | Johnson | A61N 1/05 606/41 |
| 2010/0249729 A1* | 9/2010 | Morris | A61B 17/00234 604/272 |
| 2010/0292768 A1* | 11/2010 | Sommer | A61N 1/0573 607/116 |
| 2011/0060395 A1* | 3/2011 | Cantlon | A61N 1/0509 607/116 |
| 2011/0098561 A1* | 4/2011 | Thornton | A61M 25/0054 600/431 |
| 2011/0208281 A1* | 8/2011 | Carbunaru | A61N 1/05 607/116 |

* cited by examiner

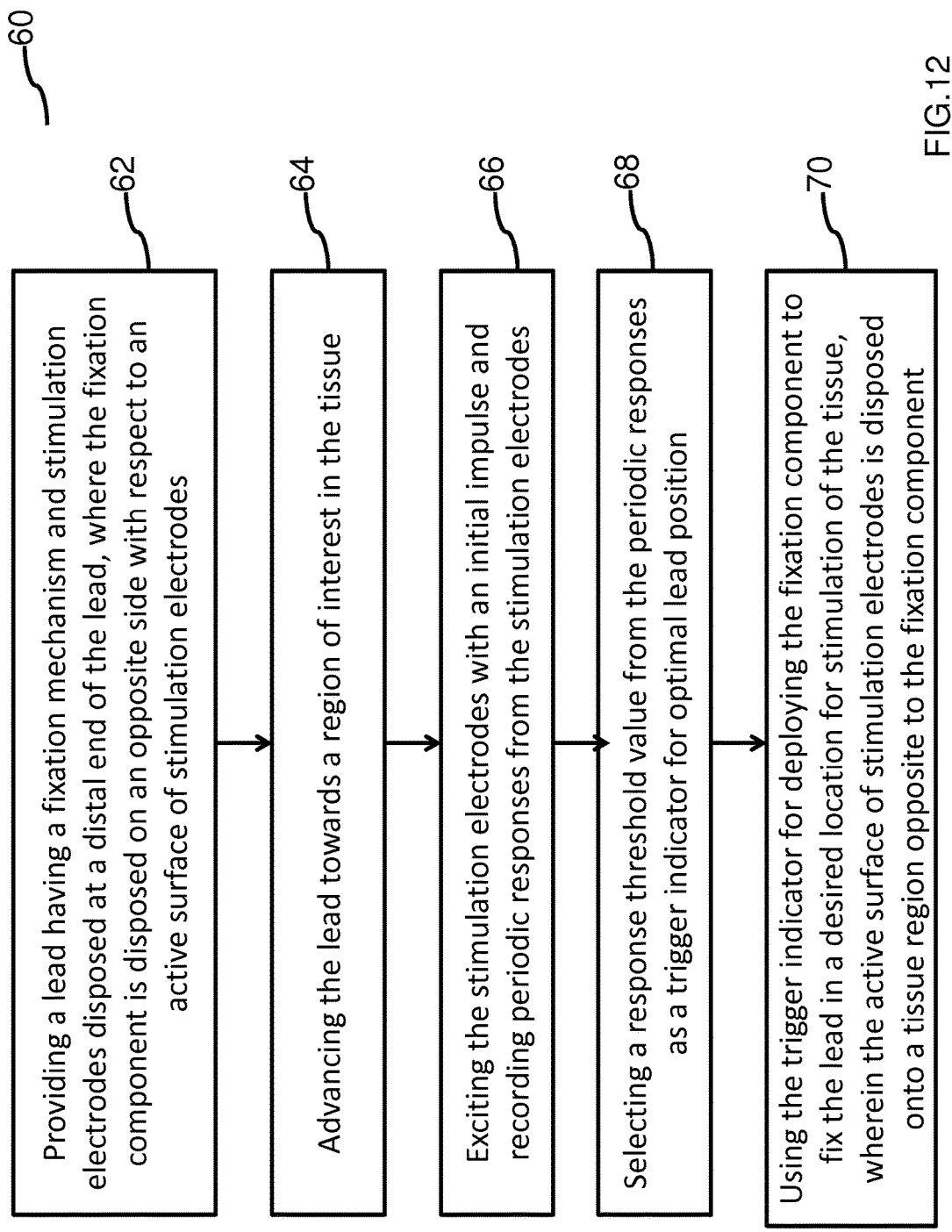

MECHANISM, SYSTEM, METHOD FOR IN VIVO LEAD FIXATION

This application is a non-provisional application for U.S. provisional application 61/611,016 that was filed on 15 Mar. 2012.

TECHNICAL FIELD

The invention relates generally to placement of leads in vivo for stimulation of a tissue and more specifically to placement and fixation of cardiac lead in the intravascular or pericardial cavitary locations.

BACKGROUND

Cardiac resynchronization therapy involves pacing the left ventricle (LV) with a pacing electrode that are disposed on a pacing lead, placed within the coronary venous system. Placement of the pacing lead is severely limited by anatomical factors, especially venous anatomy. One of the most common issue is phrenic nerve pacing, a problem that can be seen in 40% of patients who undergo this procedure. The problem of phrenic nerve pacing occurs because the phrenic nerve is attached to the parietal pericardium, and the coronary vein is an epicardial structure, just beneath the pericardium. Hence, the pacing electrode can be immediately adjacent to the nerve leading to diaphragmatic pacing, and leading to patient discomfort. Some of techniques employed for phrenic nerve avoidance include one described in U.S. Application No. 20030065365 that describes detecting diaphragmatic or other skeletal muscle contraction associated with the output of a pacing pulse. Upon detection of diaphragmatic contraction, the device may be configured to automatically adjust the pacing pulse energy and/or pacing configuration. U.S. Application No. 20130046356 describes another technique using segmented electrodes. PCT/US2005/031559 describes a technique to address electrode individually, such that each may be activated individually, or in combinations with other electrodes with the aid of the multiplexing circuits on the Integrated Circuits. Some other techniques include electronic repositioning (simply choosing a different vector). As one skilled in the art would know these techniques require further electronic hardware or post-processing software and do not remove the risk of pressing the phrenic nerve.

Other factors that limit lead positioning include markedly elevated pacing thresholds at certain locations. Hence, more often than not, the lead is not placed at the desired location. Rather, the lead is placed at the site where the vessel anatomy allows placement. Besides anatomical limitations, lead positioning is also often limited by technical factors including accessibility, & lead stability within the appropriate region of the appropriate vein.

Techniques for appropriate placement of cardiac lead in the intravascular or pericardial cavitary locations such as left ventricle (LV) are continuing to be developed. Some techniques currently used include advancing the lead distally into a progressively narrowing vein until it can not be advanced any further, another technique includes a mechanism where, upon removal of the stylet, the lead assumes a predetermined S-shape, and some other techniques employ plastic lobes along with the lead that expand upon deployment in the cardiac region.

Despite these advancement, the failure rate of cardiac lead implantation still averages up to 10% in most large studies. And such issues are faced even while using the lead for stimulating other regions of the body such as specific nerves in the nervous system. Thus there is a need for improved technique and system to ensure stimulation electrodes are positioned only at region of interest.

BRIEF DESCRIPTION

In one aspect, the invention provides a lead fixation mechanism disposed at a distal end of a lead having stimulation electrodes for stimulation of a tissue. The lead fixation mechanism comprises a fixation component disposed on an opposite side with respect to an active surface of the stimulation electrodes at a distal end of the lead. When deployed, the lead fixation mechanism disposes the active surface of stimulation electrodes onto a tissue region opposite to the fixation component.

In another aspect, the invention provides a system for optimally positioning a lead for stimulation of a tissue. The system comprises a transceiver module coupled to the lead, wherein the lead comprises stimulation electrodes and a fixation component disposed on a distal end of the lead, wherein an active surface of the stimulation electrodes is on an opposite side with respect to the fixation component. The transceiver module is configured to send input electrical activation signal to the stimulation electrodes and to receive an electrical response from the stimulation electrodes. The system further comprises a processor to process the electrical response from the stimulation electrodes and to generate an indication of optimal lead position based on a response threshold value. The indication from the processor is used to trigger deployment of the fixation component to fix the lead in a desired location for stimulation of the tissue.

In yet another aspect, the invention provides a method for fixing a lead in-vivo for stimulation of a tissue. The method comprises steps for providing a lead having a fixation mechanism and stimulation electrodes disposed at a distal end of the lead, wherein the fixation component is disposed on an opposite side with respect to an active surface of stimulation electrodes. According to the method the lead is advanced towards a region of interest in the tissue. Next, the stimulation electrodes are excited with an initial impulse and periodic responses from the stimulation electrodes are recorded. Method then includes a step for selecting a response threshold value from the periodic responses as a trigger indicator for optimal lead position. Then as a next step, the trigger indicator is used for deploying the fixation component to fix the lead in a desired location for stimulation of the tissue, where the active surface of stimulation electrodes is disposed onto a tissue region opposite to the fixation component.

DRAWINGS

These and other features, aspects, and advantages of the present invention will become better understood when the following detailed description is read with reference to the accompanying drawings in which like characters represent like parts throughout the drawings, wherein:

FIG. 12 is a flowchart representation for a method for optimally positioning a lead for stimulation of a tissue according to another aspect of the invention.

DETAILED DESCRIPTION

As used herein and in the claims, the singular forms "a," "an," and "the" include the plural reference unless the context clearly indicates otherwise.

Some of the anatomical terms used herein are described briefly for general understanding.

Pericardium is a tough double layered membrane which covers the heart. The space between the two layers of it is filled with a pericardium fluid which protects the heart from any kind of external jerk or shock. There are two layers to the pericardial sac: the outermost fibrous pericardium and the inner serous pericardium. The serous pericardium, in turn, is divided into two layers, the parietal pericardium, which is fused to and inseparable from the fibrous pericardium, and the visceral pericardium, which is part of the epicardium. The epicardium is the layer immediately outside of the heart muscle proper (the myocardium).

The pericardial cavity (or pericardial space) is a potential space between the parietal pericardium and visceral layer.

The phrenic nerve is a nerve that originates in the neck and passes down between the lung and heart to reach the diaphragm. It is important for breathing, as it passes motor information to the diaphragm and receives sensory information from it.

The lead described herein can be any tissue stimulation lead including but not limited to a cardiovascular lead, epicardial lead, left ventricular lead, etc.

The invention described herein provides a multifunctional lead fixation mechanism, system and method that advantageously provide multiple functionalities that include lead fixation in a desired anatomical region, and a system and method for optimal pacing (better pacing threshold and capture) for stimulating a tissue. In a specific use case related to cardiac procedures, the invention provides a mechanism for phrenic nerve avoidance, which removes the problem of diaphragmatic pacing. These aspects are described in more detail herein below.

Figure 1:
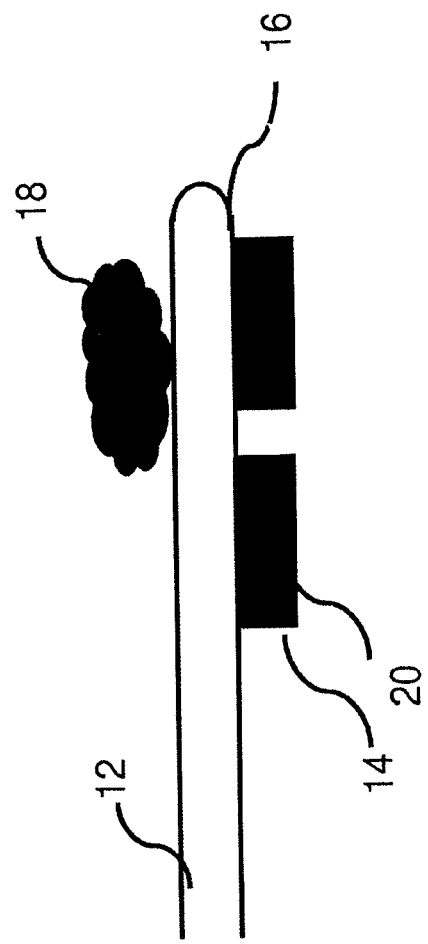
FIG. 1 is a diagrammatic representation of a lead and a fixation mechanism according to one embodiment.

In an exemplary embodiment as shown in FIG. 1, a lead 12 has stimulating electrodes 14 at a distal end 16 of the lead for stimulation of a tissue. A lead fixation mechanism comprises a lead fixation component 18 that is disposed at the distal end 18 of the lead. As is seen in FIG. 1, the fixation component is disposed on an opposite side with respect to an active surface 20 of the stimulation electrodes. Such placing of the stimulating electrodes and the fixation component provide unique advantages for fixing the lead in a region of interest, as will be explained in relation to cardiac pacing.

When the lead fixation mechanism is deployed for fixing the lead, it disposes the active surface of stimulation electrodes onto a tissue region opposite to the fixation component.

It may be appreciated by those skilled in the art that in an exemplary embodiment the fixation component is disposed on a partial portion of a lead circumference, for example covering only one half of the circumference of the lead. Thus the lead fixation component and the stimulating electrodes are in non-contact arrangement with each other.

The fixation component as described herein may be selected from a biocompatible sponge made of material such as but not limited to silicone, polymer tines, self expanding nitinol structure, a hydrogel, plastic/polyurethane lobe, combinations or other available fixation component traditionally used in pacing leads. The term hydrogel as used herein refers to a superabsorbent material comprising a structure or matrix that is typically a natural or synthetic polymer that expands in volume and size upon exposure to body fluids. In the dry state, it is relatively thin. With hydration, it expands and the desirable increase in volume is approximately 40-50%. The following are typical examples of hydrogels that may be used: poly 1-hydroxyethyl methacrylate, polymethacrylic acid, poly (N,N dimethyl-aminoethyl methacrylate), polyacrylamide, poly (N-vinyl pyrrolidone), polyvinyl alcohol, polyethylene oxides, hydrolyzed polyacrylonitriles, anionic and cationic hydrogels, or composites or copolymers of one or more of these hydrogels together with other suitable biocompatible materials such as silicone or polyurethane.

Figure 2:
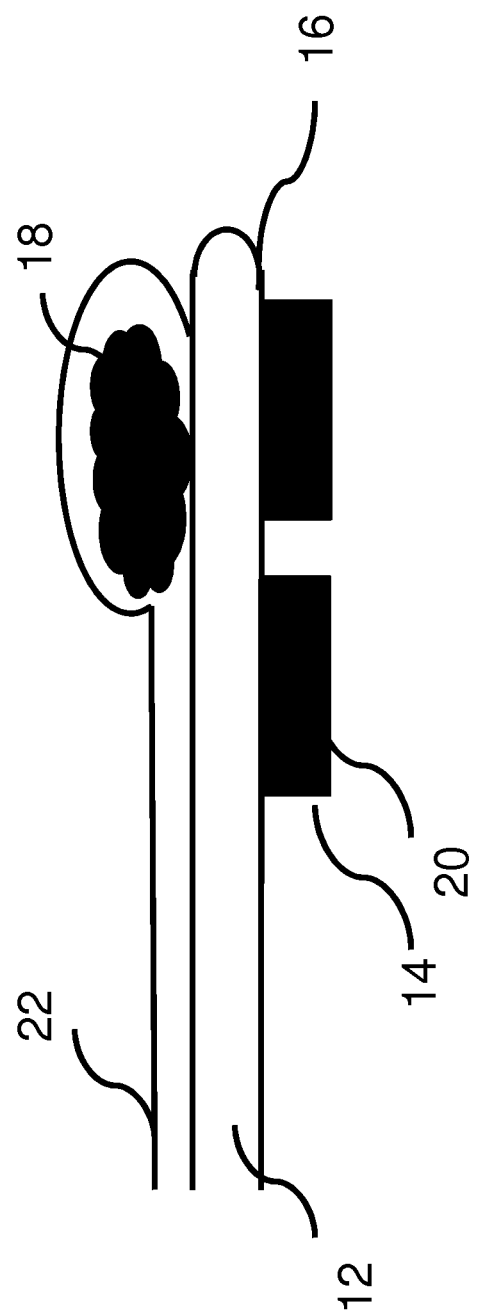
FIG. 2 is a diagrammatic representation of a fixation component provided with a sheath according to another embodiment.

It would be appreciated by those skilled in the art that the material used for fixation component will be bio-compatible. Some of the materials used as fixation component expand either by contact with bodily fluids or by application of pressure. In a specific example, the fixation component is covered by a retractable polymer sheath 22 as shown in FIG. 2, and for deployment of the fixation component for fixing the lead 12, the polymer sheath is retracted.

Figure 3:
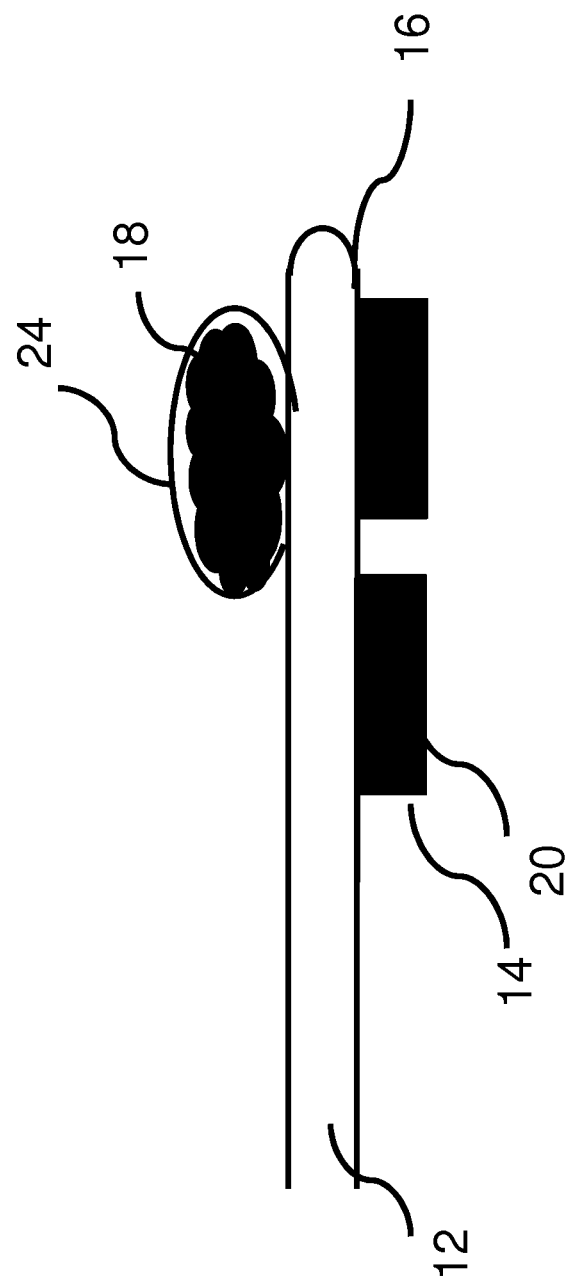
FIG. 3 is a diagrammatic representation of a fixation component provided with a dissolvable film according to another embodiment.
Figure 4:
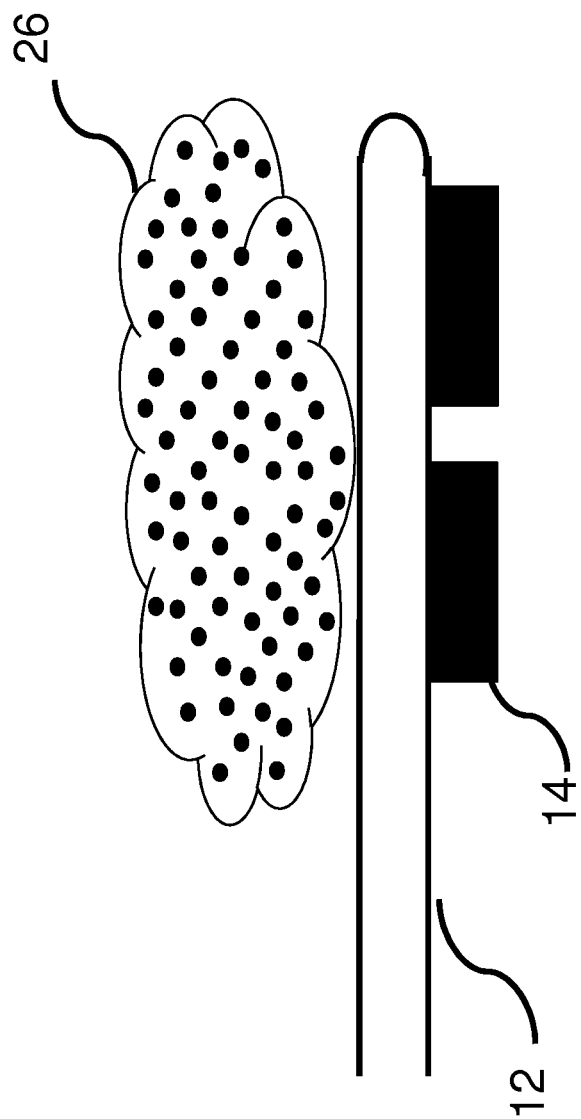
FIG. 4 is a diagrammatic representation of a fixation component in an expanded state according to one embodiment.

In a specific exemplary embodiment that uses the biocompatible sponge as the fixation component, the biocompatible sponge is provided in a compressed state and in one example, is encased within a dissolvable film 24 as shown in FIG. 3. In one example the dissolvable film is made of bio-compatible material such as starch or cellulose. For fixing the lead, the dissolvable film is dissolved through contact with bodily fluids such as blood, or by mechanical pressure, and the biocompatible sponge expands to appropriately fix the lead against the desired location. The expanded biocompatible sponge 26 is shown in FIG. 4.

It would be appreciated by those skilled in the art that the features of polymer sheath, dissolvable film, are non-limiting features, and other techniques known to one skilled in the art that serve to provide protection to the fixation component, and prevention of premature expansion of the fixation component may be used.

Figure 5:
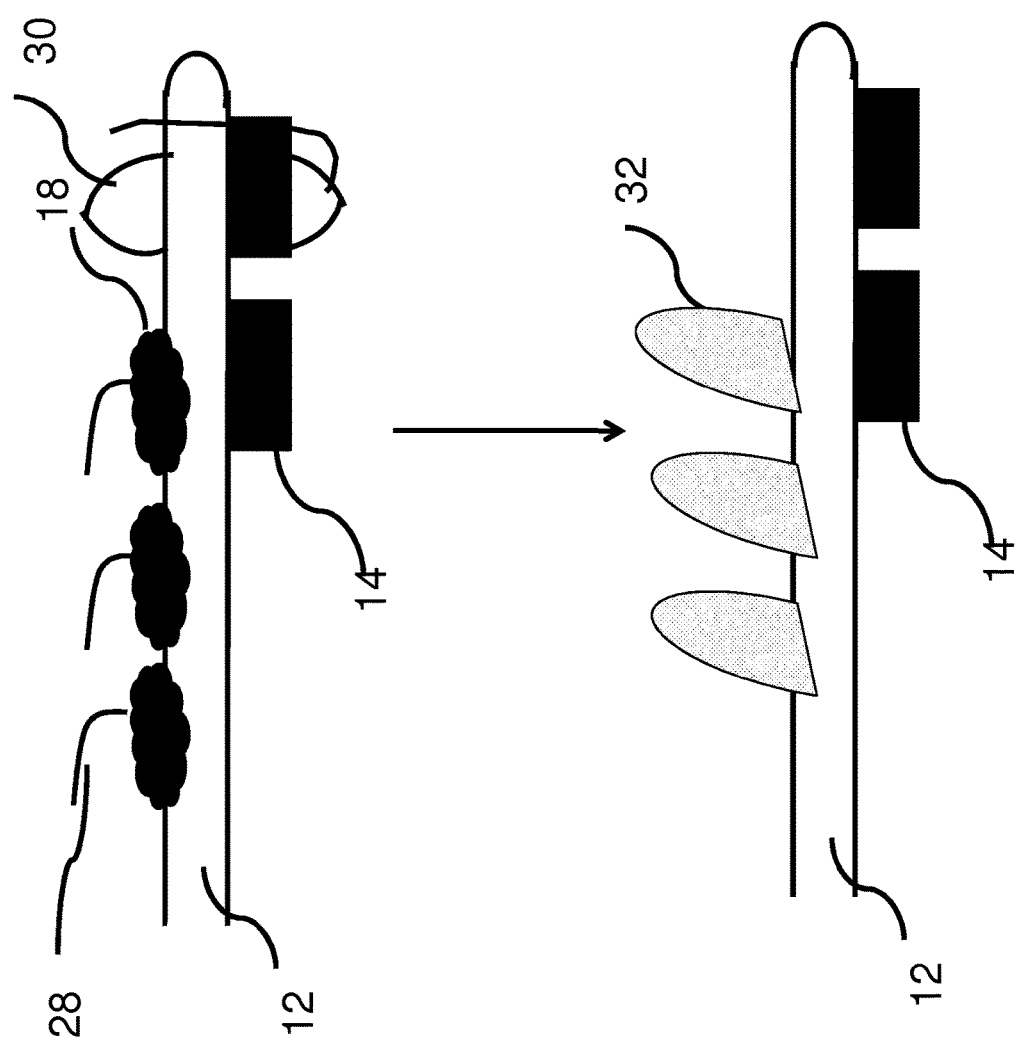
FIG. 5 is a diagrammatic representation of additional features for the fixation component according to another embodiment.

In another exemplary embodiment, the fixation component is coated with a bio adhesive material that is additionally provided as one or more spines, as shown by reference numeral 28 in FIG. 5. Collapsible wings 30 may additionally be provided that have a predefined tortuosity to prevent the lead from rolling over in a region of interest. The spines and fixation component such as the biocompatible sponge expand to provide adhesion spines 32 as shown in FIG. 5. The bio adhesive material may be selected from at least one of starch, cellulose, talc, or combinations thereof.

Specific embodiments may also include features such as a locking key mechanism of a lead stylet and lead tip (not shown), as would be known to one skilled in the art, for rotation of the lead.

In the embodiments described herein, the stimulation electrodes could be shaped as semi-circular ring, quadrant, or fully circular rings. Further, the stimulation electrodes in one example are formed by selectively metalizing a polymer surface, as would be known to one skilled in the art, to provide the active surface of the stimulation electrodes, as shown by the stimulation electrode embodiments 14 in FIG. 6. Reference numeral 46 indicates the polymerized surface and the reference numeral 48 indicates the active surface (discussed in reference with FIG. 1) of the stimulation electrodes 14.

In a specific embodiment, the lead fixation mechanism as described hereinabove further includes radio opaque markers (not shown) positioned on the lead to identify an orientation of the lead fixation component with respect to the tissue region. The radio opaque markers may be provided as combination of rings, dots and longitudinal lines that positively identify in and out of plane orientation to position the lead appropriately. This is advantageous, as the stimulation electrodes can be appropriately positioned in the region of interest based on the orientation of the lead.

Figure 6:
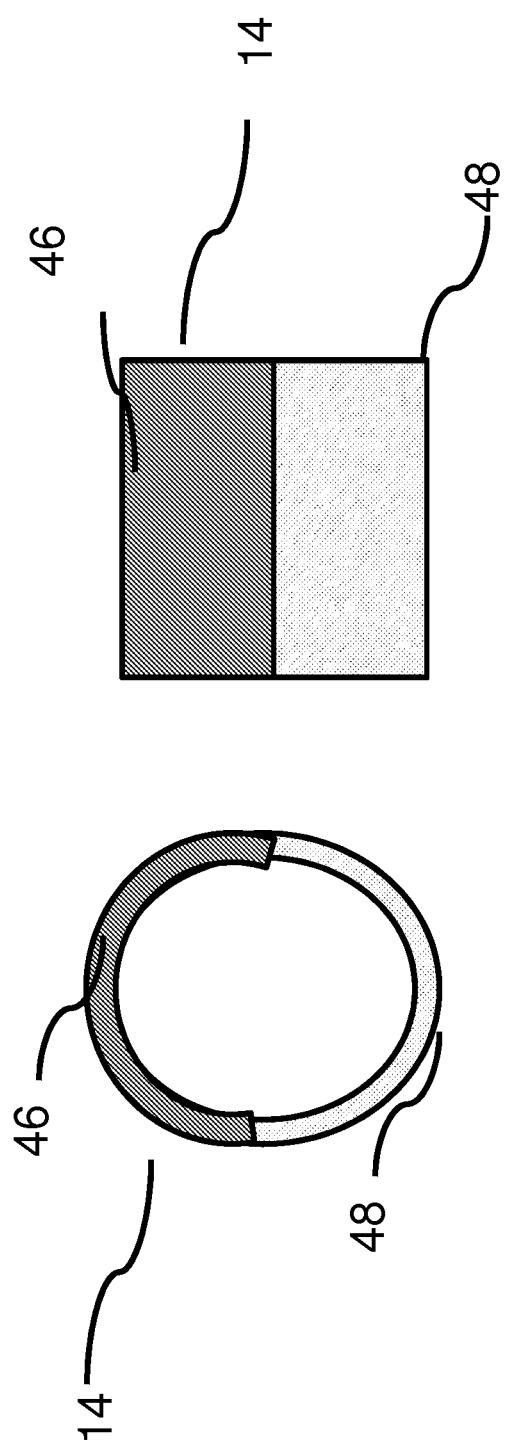
FIG. 6 is a diagrammatic representation of stimulation electrodes used in the embodiments.
Figure 7:
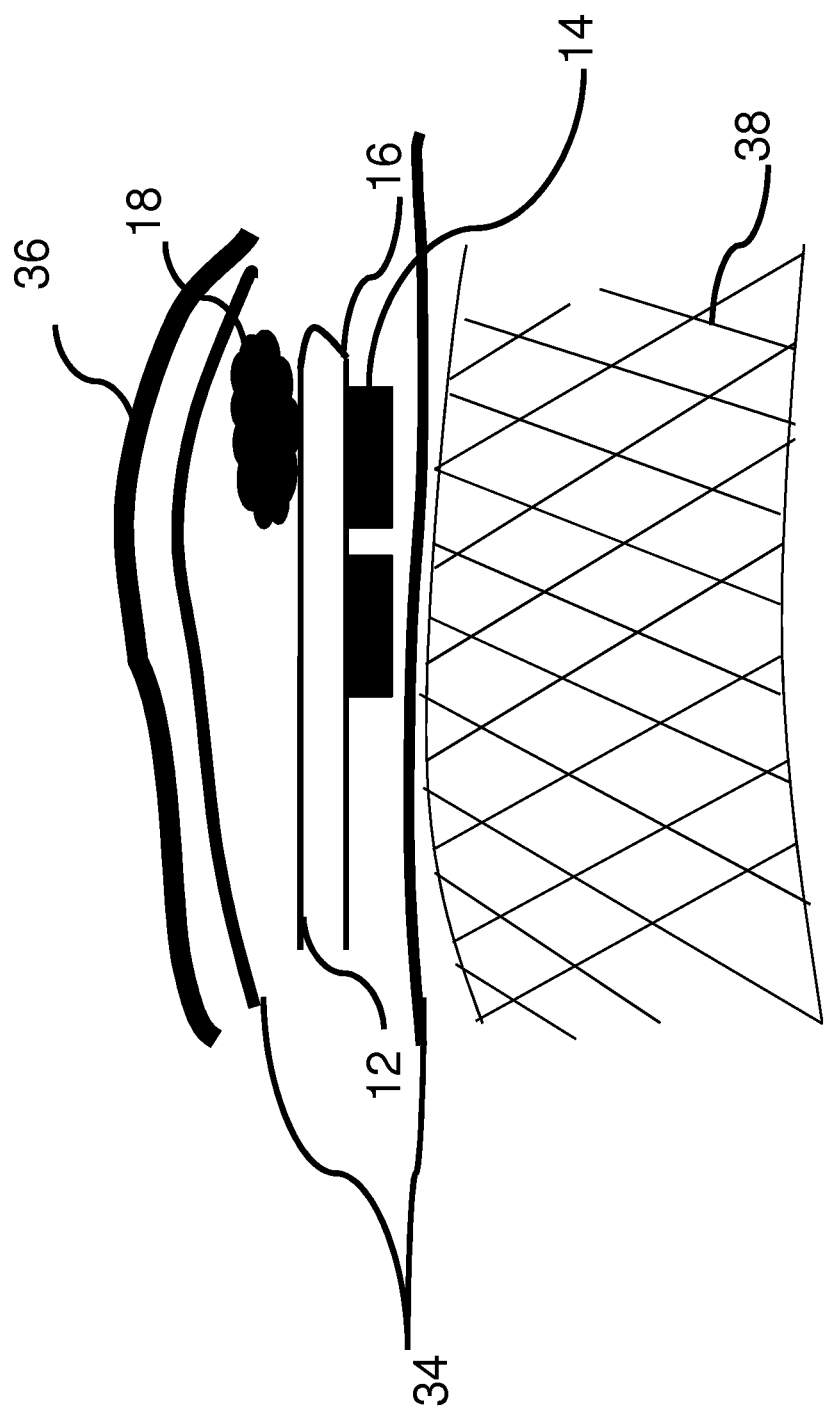
FIG. 7-10 are diagrammatic representations of a lead with the fixation component of the invention used for cardiac procedures.
Figure 8:
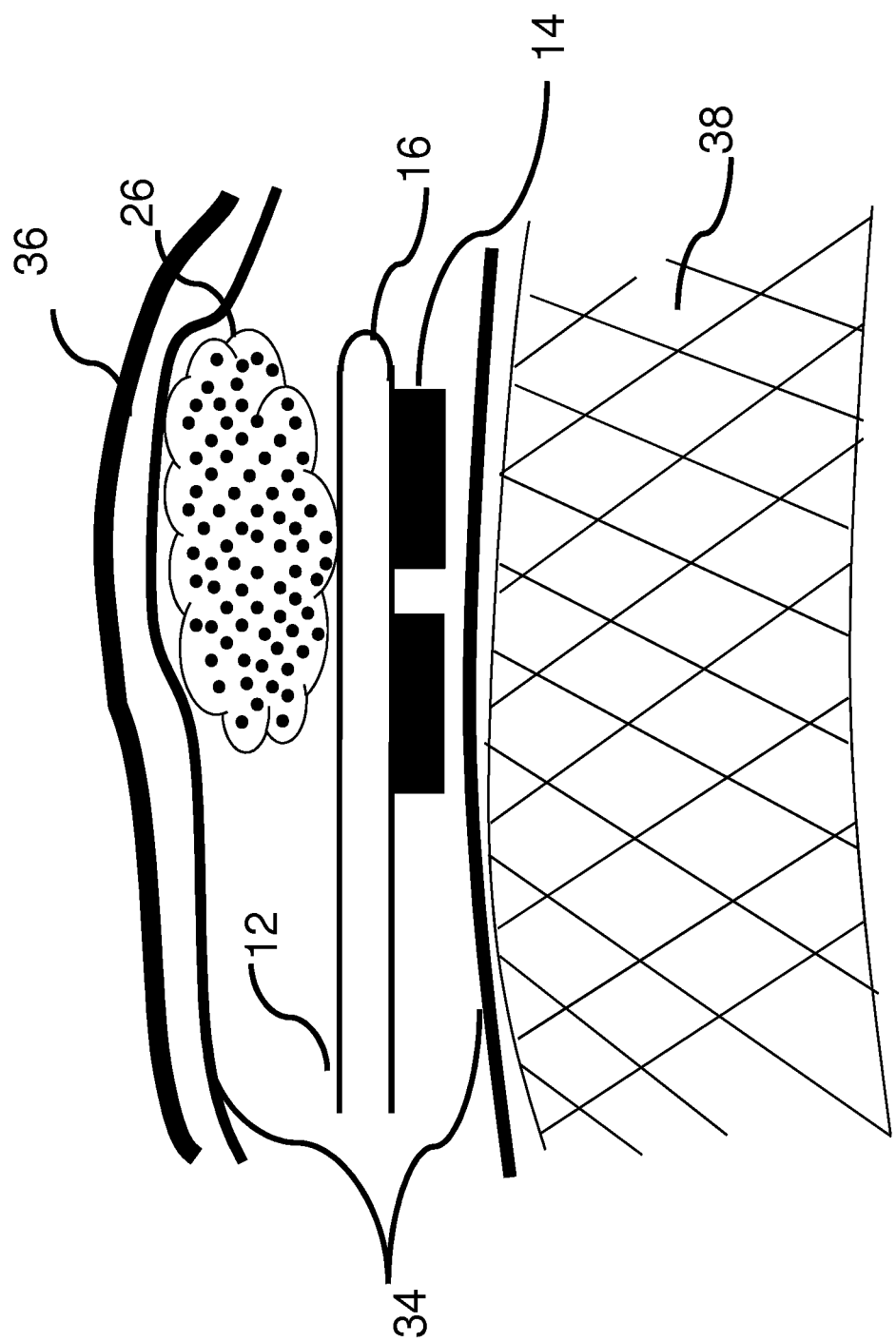

The lead fixation mechanism as described herein is useful for stimulating different anatomical regions for example, in cardiac resynchronization therapy that involves pacing the left ventricle (LV), where the tissue is a cardiac tissue, and the lead is a pacing lead. In this specific use scenario, as shown in FIG. 6 the pacing lead 12 having the stimulating electrodes 14 and the fixation component 18 at the distal end 16 of the pacing lead, is advanced in the epicardial coronary vein 34 of the left ventricle, with the parietal pericardium 36 on one side and the mycocardium 38 on the other side. FIG. 8 shows the deployed position of the fixation component, where the fixation component expands as shown by reference numeral 26 at a fixing location to advantageously form an insulating barrier between the stimulation electrodes and pericardium region. Thus, the parietal pericardium along with the phrenic nerve is pushed away from the stimulation electrodes. The active surface of the stimulating electrodes face mycocardium, while the fixation component faces the parietal pericardium. It would be known to one skilled in the art that the phrenic nerve runs along with the pericardiophrenic artery and vein as the pericardiophrenic bundle and is adherent to the parietal pericardium. By moving the pericardium away from the stimulation electrodes as explained herein, the problem of diaphragmatic pacing is also advantageously solved. Such a fixation provides distinct advantageous for pacing as lower pacing thresholds can be used. In contrast when the inactive surface (on the side where the fixation component is present) is in contact with the myocardium it will give higher pacing impedance and thresholds, and additionally, there may be no capture (i.e. cannot pace). By rotating the lead as described in the embodiments of the invention, the active surface can brought to face the mycocardium, and optimal positioning is achieved.

Figure 9:
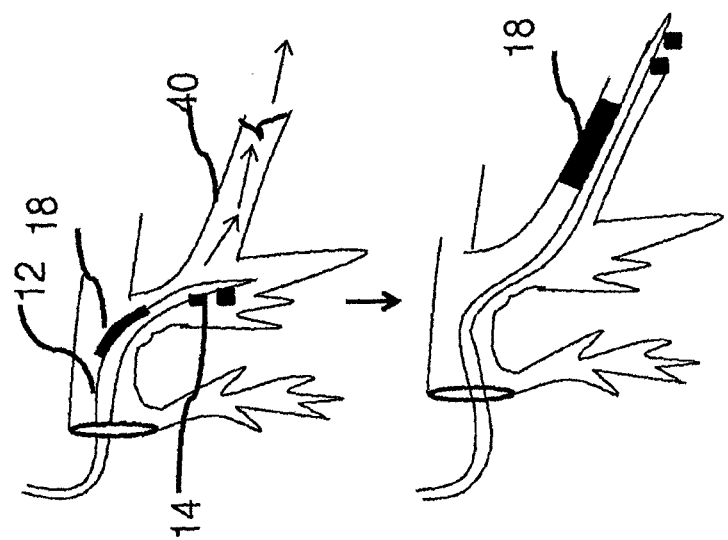
Figure 10:
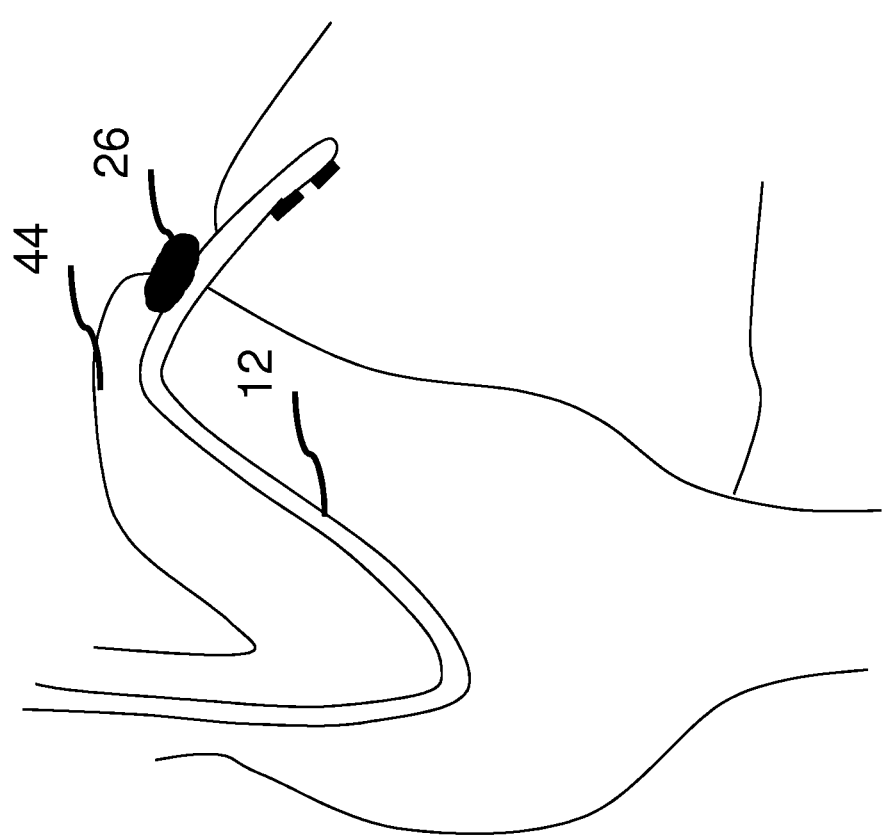

In a specific use scenario, the fixation component expands to safely perforate a cardiac vessel wall as shown in FIG. 9, or a right atrial appendage as shown in FIG. 10 or a right ventricle (RV) apex etc to provide access for the pacing lead into a pericardial cavity in the pericardium region. As shown in FIG. 9 and FIG. 10, the vessel wall 40 (FIG. 9) and right atrial appendage 44 (FIG. 10) is intentionally perforated and the pacing lead 12 is advanced through this perforation. An expanding layer of the fixation component such as, but not limited to the biocompatible sponge or hydrogel occludes the perforation site and forms a hemostatic plug (shown as reference numeral 18 in FIG. 9 and as 26 in FIG. 10). This advantageously limits the risk of bleeding. Such a fixation may also be achieved via a layer of adhesive material disposed on the fixation component. In one example the adhesive material is released as spines on the pacing lead that create pericardial inflammation where the spines attach themselves and thus fix the pacing lead, and prevent the pacing lead from moving within the cavity. Such lead fixation and placing the pacing lead in the pericardial cavity is extremely advantageous as such locations are not hindered by venous anatomy.

Figure 11:
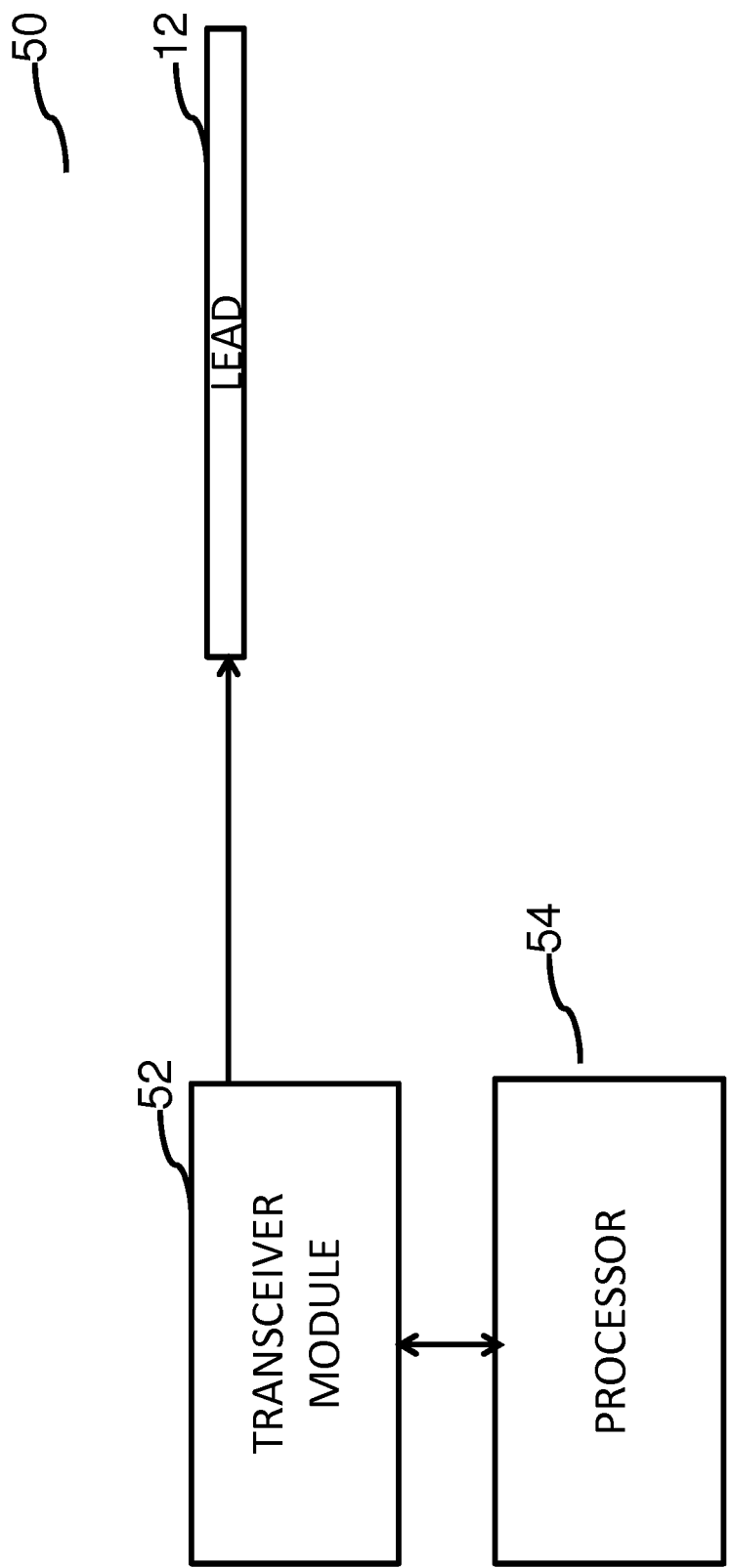
FIG. 11 is a diagrammatic representation of a system for optimally positioning a lead for stimulation of a tissue using the fixation component of FIGS. 1-6 according to another embodiment.

FIG. 11 is a diagrammatic representation of a system 40 for optimally positioning a lead for stimulation of a tissue. The system comprises a transceiver module 52 coupled to the lead 12, where the lead comprises stimulation electrodes and the fixation component disposed on the distal end of the lead, as described in detail herein above. In an exemplary embodiment, the fixation component is disposed on a partial portion of the circumference of the lead.

The transceiver module 52 is configured to send input electrical activation signal to the stimulation electrodes and to receive an electrical response from the stimulation electrodes. The system 40 further includes a processor 54 to process the electrical responses from the stimulation electrodes and to generate an indication of optimal lead position based on a response threshold value. The response threshold value as used herein corresponds to an electrical response from the stimulating electrodes when the active surface is in contact with a desired portion of the tissue. The indication from the processor is used to trigger deployment of the fixation component to fix the lead in a desired location for stimulation of the tissue. The system 50 may include additional modules that are not shown, such as but not limited to a display module to display the electrical responses, response threshold value, indication for deployment, as well as images that show the position, orientation of the lead due to the presence of radio opaque markers as described hereinabove. The system 50 may also include a communication module to transfer data from the processor to display module or to an output module, or to another communication or imaging device.

In another aspect, the invention provides a method for fixing a lead in-vivo for stimulation of a tissue a shown in flowchart 60. The method comprises, a step 62 for providing a lead with stimulating electrodes and a fixation component disposed on an opposite side with respect to an active surface of stimulation electrodes. The lead is advanced towards a region of interest in the tissue as shown by step 64. The stimulation electrodes are excited with an initial impulse at step 66 and the responses from the stimulation electrodes are recorded periodically. A response threshold value is selected from the periodic responses as a trigger indicator for optimal lead position at step 68. And at step 70, the fixation component is deployed to fix the lead in a desired location for stimulation of the tissue, where the active surface of stimulation electrodes is disposed onto a tissue region opposite to the fixation component. It may be noted here that the response threshold value corresponds to an electrical response from the stimulating electrodes when the active surface is in contact with a desired portion of the tissue.

The embodiments described hereinabove provide several advantages over the existing pacing leads and fixation methods and systems. The phrenic nerve avoidance by pressing the active surface of the stimulation electrodes against the myocardium is an important advantage that resolves diaphrammatic pacing issues. Patients who previously would have been required to have their resynchronization device turned off due to phrenic nerve capture will not face this problem with the embodiments described herein. Further, the method to optimize the pacing thresholds is uniquely provided by the invention since only the active surface of the pacing electrodes is in contact with the myocardium. It would be appreciated by those skilled in the art that when the active surface of the electrode is touching the myocardium, best or optimal pacing thresholds are achieved. The low pacing capture voltage threshold achieved by the present invention allows the advantages of low energy consumption. Additionally, it brings patients who would be at too high a voltage level for safe or effective pacing into a range where they, too, can enjoy the benefits of resynchronization therapy.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims. Also, the individual embodiments described and illustrated herein may have discrete components and features which may be readily separated from or combined with the features of any of the other several embodiments without departing from the scope or spirit of the present invention.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A fixation mechanism for a pacing lead positioned at a distal end of the pacing lead, the pacing lead having one or more stimulation electrodes that stimulate cardiac tissue when the pacing lead is advanced into an epicardial coronary vein of a left ventricle and is configured to be surrounded by a parietal pericardium with an attached phrenic nerve on one side and a myocardium on an opposite side, the fixation mechanism comprising:
   a fixation component that has an expandable portion, the expandable portion faces the parietal pericardium and is positioned on a side opposite an active surface of the one or more stimulation electrodes that faces the myocardium, wherein when the expandable portion of the fixation component expands, the expandable portion of the fixation component is configured to:
   move the parietal pericardium and the attached phrenic nerve away from the one or more stimulation electrodes,
   fix the active surface of the one or more stimulation electrodes onto a tissue region of the myocardium within the epicardial coronary vein; and
   form an insulating barrier between the parietal pericardium and the active surface of the one or more stimulation electrodes that are fixed onto the tissue region of the myocardium within the epicardial coronary vein to insulate the attached phrenic nerve from the active surface of the one or more stimulation electrodes, the insulation barrier having an impedance that is based on a position of the fixation component within the epicardial coronary vein.

2. The fixation mechanism of claim 1, wherein the fixation component is disposed on a partial portion of a lead circumference at the distal end of the pacing lead.

3. The fixation mechanism of claim 1, wherein the fixation component is composed of at least one of a biocompatible sponge, polymer tines, self expanding nitinol structure, a hydrogel and combinations thereof.

4. The fixation mechanism of claim 1, wherein the fixation component is covered by a retractable polymer sheath, and wherein the fixation component is deployed by retracting the polymer sheath.

5. The fixation mechanism of claim 1, wherein the fixation component is coated with a bio adhesive material that creates one or more spines to provide adhesion of the pacing lead in a desired location.

6. The fixation mechanism of claim 5, wherein the bio adhesive material is at least one of starch, cellulose, talc, or combinations thereof.

7. The fixation mechanism of claim 3, wherein the biocompatible sponge is covered by a dissolvable film.

8. The fixation mechanism of claim 1, wherein the one or more stimulation electrodes are at least one of semi-circular ring, quadrant, or fully circular rings.

9. The fixation mechanism of claim 1, wherein the one or more stimulation electrodes are formed by selectively metalizing a polymer surface to provide the active surface of the one or more stimulation electrodes.

10. The fixation mechanism of claim 1, further comprising radio opaque markers positioned on the pacing lead to identify an orientation of the fixation component with respect to the tissue region.

11. The fixation mechanism of claim 1, further comprising a locking key mechanism to avoid rotation of the pacing lead.

12. The fixation mechanism of claim 1, wherein the fixation component expands at a fixing location to form the insulating barrier between the active surface of the one or more stimulation electrodes and the parietal pericardium.

13. The fixation mechanism of claim 1, wherein the fixation component expands and does not perforate a cardiac vessel wall to provide access for the pacing lead into a pericardial cavity in a region of the parietal pericardium.

14. The fixation mechanism of claim 1, wherein the one or more stimulation electrodes are only positioned on a side that faces the myocardium.

15. The fixation mechanism of claim 1, wherein the pacing lead is configured to control the impedance of the insulating barrier by rotating and positioning the active surface of the one or more stimulation electrodes to face the myocardium and positioning the fixation component to face the parietal pericardium with the attached phrenic nerve.

16. The fixation mechanism of claim 1, wherein the fixation component expands within a circumference of the epicardial coronary vein.

17. The fixation mechanism of claim 1, wherein the fixation component is made of a plastic or polyurethane lobe that is configured to be expandable and to fix the pacing lead in a particular position.

* * * * *